US010456376B2

(12) United States Patent
Shin et al.

(10) Patent No.: US 10,456,376 B2
(45) Date of Patent: Oct. 29, 2019

(54) USE OF CARBAMATE COMPOUND IN ORDER TO PREVENTATIVELY TREAT HEADACHES

(71) Applicant: SK BIOPHARMACEUTICALS CO., LTD., Gyeonggi-do (KR)

(72) Inventors: Hye Won Shin, Gyeonggi-do (KR); Yoon Kyung Park, Gyeonggi-do (KR)

(73) Assignee: SK BIOPHARMACEUTICALS CO., LTD., Gyeonggi-Do (KR)

(*) Notice: Subject to any disclaimer, the term of this patent is extended or adjusted under 35 U.S.C. 154(b) by 0 days.

(21) Appl. No.: 16/302,842

(22) PCT Filed: May 18, 2017

(86) PCT No.: PCT/KR2017/005171
§ 371 (c)(1),
(2) Date: Nov. 19, 2018

(87) PCT Pub. No.: WO2017/200316
PCT Pub. Date: Nov. 23, 2017

(65) Prior Publication Data
US 2019/0216780 A1    Jul. 18, 2019

(30) Foreign Application Priority Data
May 19, 2016    (KR) .................. 10-2016-0061374

(51) Int. Cl.
*A61K 31/41*    (2006.01)
*A61P 25/06*    (2006.01)

(52) U.S. Cl.
CPC .............. *A61K 31/41* (2013.01); *A61P 25/06* (2018.01)

(58) Field of Classification Search
CPC ................................. A61K 31/41; A61P 25/06
USPC ........................................................ 514/381
See application file for complete search history.

(56) References Cited

U.S. PATENT DOCUMENTS

| 3,415,840 | A | 12/1968 | Wolf | |
|---|---|---|---|---|
| 7,598,279 | B2 * | 10/2009 | Choi | C07D 249/04 514/281 |
| 2010/0323410 | A1 | 12/2010 | Lim et al. | |
| 2011/0111467 | A1 | 5/2011 | Lim et al. | |

FOREIGN PATENT DOCUMENTS

| KR | 101286499 B1 | 7/2013 |
|---|---|---|
| WO | WO-2006/112685 A1 | 10/2006 |
| WO | WO-2010/150946 A1 | 12/2010 |
| WO | WO-2011/045380 A1 | 4/2011 |

OTHER PUBLICATIONS

Akerman, et al. (2005) "Topiramate inhibits cortical spreading depression in rat and cat: impact in migraine aura." *Clinical Neuroscience and Neuropathology—Neuroreport*, 16(12)1383-1387, (Aug. 22, 2005).
Ayata, et al. (2006) "Suppression of Cortical Spreading Depression in Migraine Prophylaxis." *Ann Neurol*, 59:652-661.
Edvinsson, et al. (2012) "Basic mechanisms of migraine and its acute treatment.", *Pharmacology & Therapeutics*, 136:319-333.
Hoffmann, et al. (2010) "Oxcarbazepine does not suppress cortical spreading depression.", *Cephalalgia*, 31(5) 537-542.
International Search Report (ISR) issued in International Patent Application No. PCT/KR2017/005171, dated Aug. 21, 2017 with English Translation.
Jackson, et al., (2015) "A comparative effectiveness meta-analysis of drugs for the prophylaxis of migraine headaches.", *PLOS ONE*, DOI:10.1371/journal.pone.0130733, Jul. 14, 2015) pp. 1-60.
Karakurt, et al. (2001) "Synthesis of some 1-(2-naphthyl)-2-(imidazole-1-yl)ethanone oxime and oxime ether derivatives and their anticonvulsant and antimicrobial activities.", *Eur. J. Med. Chem.*, 36:421-433.
Krymchantowski, et al. (2002) "New and Emerging Prophylactic Agents for Migraine.", *CNS Drugs*, 16(9):611-634.
Mathew, N.T. (1993) "Transformed migraine." *Cephalalgia*, 13(suppl 12):78-83. Oslo. ISSN 0800-1952.
Mathew, N.T. (2011) "Pathophysiology of Chronic Migraine and Mode of Action of Preventive Medications." *Headache*, 51(S2):84-92.
Noseda, et al. (2013) "Migraine pathophysiology: Anatomy of the trigeminovascular pathway and associated neurological symptoms, cortical spreading depression sensitization, and modulation of pain." PAIN 8911, (Aug. 13, 2013), pp. 1-10. http://dx.doi.org/10.1016/j.pain.2013.07.021.

* cited by examiner

*Primary Examiner* — Yevgeny Valenrod
(74) *Attorney, Agent, or Firm* — Harness, Dickey & Pierce, P.L.C.

(57) ABSTRACT

The present invention relates to a pharmaceutical composition for preventatively treating headaches, containing: a carbamate compound of chemical formula 1 or a pharmaceutically acceptable salt, solvent or hydrate thereof; and a pharmaceutically acceptable carrier. According to the present invention, the pharmaceutical composition can effectively prevent a headache, more specifically, headaches caused by cortical spreading depression, and particularly, chronic headaches including migraines.

11 Claims, 3 Drawing Sheets

USE OF CARBAMATE COMPOUND IN ORDER TO PREVENTATIVELY TREAT HEADACHES

CROSS-REFERENCE TO RELATED APPLICATIONS

This application is a national phase application of PCT Application No. PCT/KR2017/005171, filed on May 18, 2017, which claims priority to Korean Patent Application No. 10-2016-0061374, filed on May 19, 2016. The entire disclosure of the applications identified in this paragraph is incorporated herein by reference.

FIELD

The present invention relates to use of a carbamate compound of the following Formula 1 for the purpose of preventing the occurrence of headaches including migraine, by administering a pharmaceutical composition comprising said carbamate compound:

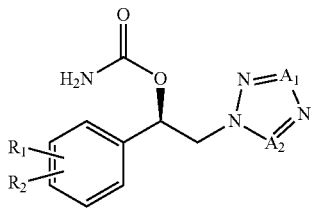

[Formula 1]

wherein,
$R_1$, $R_2$, $A_1$ and $A_2$ are as defined herein.

BACKGROUND

Migraine is a common disease with a worldwide prevalence rate of 8 to 18%. It occurs more frequently in women than in men, and can occur in both children and adults. Symptoms of migraine include not only headaches but also accompanying symptoms such as nausea, vomiting, photosensitivity, hypersensitivity to sound and hypersensitivity to odor, which are obstacles to physical activity. Such migraine-related disorders cause socio-economic losses worldwide and seriously hamper the quality of life (Krymchantowski et al., New and emerging prophylactic agents for migraine, CNS Drugs, 2002; Jackson et al., A comparative effectiveness meta-analysis of drugs for the prophylaxis of migraine headaches, PLOS ONE, 2015).

Although the pathological mechanism of migraine has not been fully understood until now, it is believed that the electrochemical imbalance in the brain due to the excitability of excessive cranial nerve caused by various environmental and intrinsic factors will act as a cause of migraine. The electrochemical imbalance induces cortical spreading depression (CSD) to stimulate the trigeminal nervous system, resulting in inflammation of the nerve periphery and vasodilation of the meninges, which are thought to cause headaches (Noseda et al., Migraine pathophysiology: anatomy of the trigeminovascular pathway and associated neurological symptoms, cortical spreading depression, sensitization, and modulation of pain. Pain, 2013; Edvinsson et al., Basic mechanisms of migraine and its acute treatment, Pharmacol Ther., 2012).

Drug treatment for migraine is divided into acute abortive treatment (acute phase treatment) and preventive treatment (prophylactic treatment). Acute abortive treatment is used for the purpose of symptom relief at the occurrence of migraine. Drugs used for acute abortive treatment include simple analgesics such as nonsteroidal anti-inflammatory drugs (NSAID) in cases of mild migraine attacks, and the use of migraine specific drugs such as Triptan should be considered in cases where patients do not respond to simple analgesics.

When using drugs for acute abortive treatment, care should be taken to avoid drug overdose. Triptan contracts the cardiovascular system, and thus it is hardly prescribed to patients with cardiovascular disease. Prophylactic treatment is used for the purpose of reducing the frequency of occurrence or the intensity of migraine attacks during the administration of the medication. Prophylactic treatment should be applied in the following cases: when daily life is interrupted by repeated migraine attacks despite acute abortive treatment; when there is a concern about overuse of acute phase drugs due to the occurrence of headaches at the frequency of twice or more a week or frequent headaches; when the patient exhibits severe side effects to acute phase drugs or if the acute phase drug is contraindicated; when the patient prefers prophylactic treatment; when the patient has a long duration of headaches; and when the patient suffers from uncommon migraine, such as hemiplegia migraine, basal type migraine, migraine with persistent aura, or migraine type cerebral infarction (J. L. Jackson et al., A comparative effectiveness meta-analysis of drugs for the prophylaxis of migraine headaches, PLOS ONE, 2015). Valproate has been used to prevent migraine, but it is known to have side effects such as liver damage and congenital malformations.

A variety of drugs have been used for the treatment or prevention of migraine, but there are still limitations in their use due to the lack of satisfactory level of drug response or side effects. Hence, there is still a need for new drugs with improved efficacy and side effects. In particular, in patients with frequent migraine attacks and severe symptoms, it is more necessary to prevent migraine through complete elimination or persistent prevention of additional attack of migraine, rather than to alleviate the occurring symptoms, and it is required to prevent migraine without serious side effects.

DISCLOSURE

Problem to be Solved

The present invention is intended to provide a method for the prophylactic treatment of headaches, more particularly chronic headaches including headaches due to cortical spreading depression (CSD), especially migraine headaches.

The present invention is also intended to provide the use of a carbamate compound of the following Formula 1, or a pharmaceutically acceptable salt, solvate or hydrate thereof, for the prophylactic treatment of headaches, more particularly chronic headaches including headaches due to cortical spreading depression (CSD), especially migraine headaches:

[Formula 1]

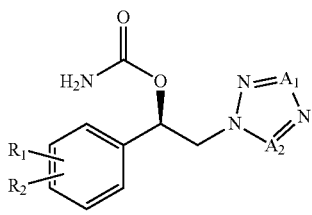

wherein,

R₁, R₂, A₁ and A₂ are as defined herein.

Technical Solution to the Problem

The present invention provides a medicament for the prophylactic treatment of headaches, comprising a therapeutically effective amount of a carbamate compound of the following Formula 1, or a pharmaceutically acceptable salt, solvate or hydrate thereof:

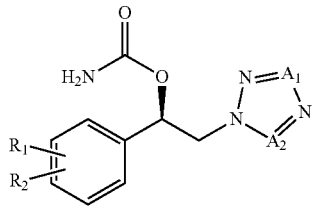

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prophylactic treatment of headaches, comprising a therapeutically effective amount of the carbamate compounds of the above Formula 1, or a pharmaceutically acceptable salt, solvate or hydrate thereof, and one or more of a pharmaceutically acceptable carrier.

In addition, the present invention provides a method for prophylactically treating headaches in a subject, comprising administering a therapeutically effective amount of the carbamate compounds of the above Formula 1, or a pharmaceutically acceptable salt, solvate or hydrate thereof to the subject. In one embodiment, the present invention provides a method for reducing or eliminating the frequency or intensity of headaches in a subject, comprising administering a therapeutically effective amount of the carbamate compounds of the above Formula 1, or a pharmaceutically acceptable salt, solvate or hydrate thereof to the subject.

In addition, the present invention provides the use of the carbamate compounds of the above Formula 1, or a pharmaceutically acceptable salt, solvate or hydrate thereof for the prophylactic treatment of headaches.

In one embodiment of the present invention, in the above Formula 1, R1 and R2 are each independently selected from the group consisting of hydrogen, halogen and C1-C8 alkyl.

In one embodiment, the halo C1-C8 alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

[Formula 2]

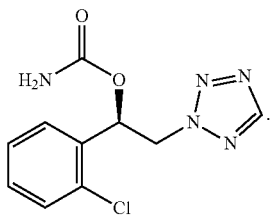

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the present invention can be chemically synthesized by any of the methods described in the above documents, but the methods are merely exemplary ones, and the order of the unit operation and the like may be selectively changed if it is necessary. Hence, the above methods are not intended to limit the scope of the invention.

According to one embodiment of the present invention, the compounds of the present invention can be used for the prophylaxis (prevention) of headaches and/or conditions associated with cortical spreading depression (CSD) and/or caused by cortical spreading depression (CSD), particularly chronic headaches such as migraine.

Cortical spreading depression (CSD) is a secondary phenomenon caused by excessive excitability of the cranial nerve and is known as a trigger phenomenon that causes chronic headaches including migraine. Thus, inhibition of cortical spreading depression (CSD) can prevent the occurrence of chronic headaches including migraine, and it has been proven in several reports that drugs that can prevent an artificially induced cortical spreading depression (CSD) in experimental animals could prevent human migraine, especially migraine with aura and chronic headaches (Ayata et al., Suppression of cortical spreading depression in migraine prophylaxis, Ann Neurol. 2006; Mathew, Pathophysiology of chronic migraine and mode of action of preventive medications, Headache. 2011; Akerman & Goadsby, Topiramate inhibits cortical spreading depression in rat and cat: impact in migraine aura, Neuroreport. 2005; Hoffmann et al., Oxcarbazepine does not suppress cortical spreading depression, Cephalalgia. 2011).

"Chronic daily headache (CDH)" consists of two main categories, i.e., long-term persistent headache (long-lasting headache) and short-term persistent headache (short-lasting headache), each of which includes the following clinical subtypes. Long-lasting headaches (i.e., duration of illness over 4 hours or more) include transformed migraine (TM), chronic tension-type headaches, new daily persistent headaches, hemicrania continua, and analgesic round headaches. Short-lasting headaches (i.e., duration of illness of less than 4 hours) include chronic cluster headaches, chronic paroxysmal hemicrania, hypnic headaches, and idiopathic stabbing headaches (Mathew, Cephalalgia 13 (suppl 12):78-83 (1993)).

The term "migraine" is used herein in its broadest sense to refer to the headache disease, disorder and/or condition according to the medical definition of migraine as defined by the International Headache Society. Therefore, the term includes so-called general migraine (migraine normally not associated with aura); classical migraine (migraine with aura); chronic migraine (migraine that occurs over a longer time interval); so-called vascular headache; severe migraine; cluster headache; hemiplegic migraine; basal migraine; chronic daily headache; all migraine syndromes (e.g., pain, nausea, phonophobia, photophobia); retinal migraine; pediatric migraine; status migrainosus; transformed migraine; drug abuse headache; migraine prodrome; and any other recurrent and/or chronic headache or headache symptoms that would be generally known to those skilled in the art. Migraine is a recurrent headache that can be unilateral or bilateral.

The term "prevention or prophylaxis" or "prophylactic treatment" as used herein means reducing or eliminating the frequency or intensity of headaches or migraine by administering a drug to a patient with headaches or migraine, or means inhibiting the occurrence of such a disease or condition in a person who tends to be susceptible to said disease or condition.

This prophylactic therapy reduces the excitability of sensitive brain and blood vessels in migraine patients and thus increases the threshold for migraine attacks to prevent the occurrence of cortical spreading depression (CSD), stabilize the nervous system, inhibit the activation of the trigeminal nervous system, strengthen the anti-pain system, block nerve inflammation and prevent central sensitization. These mechanisms can reduce the frequency of migraine attacks, intensity and duration of the pain, improve response to acute phase drugs, and improve the quality of life of patients.

The dosage of the present compounds for the prophylactic treatment of the disease may typically vary depending on the severity of the disease, the body weight and the metabolic status of the subject. A "therapeutically effective amount" for an individual patient refers to an amount of the active compound or pharmaceutical formulation sufficient to achieve the desired pharmacological effect, i.e., the prophylactic therapeutic effect as described above. The therapeutically effective amount of the compounds of the present invention is preferably 10 to 500 mg, more preferably 20 to 300 mg, 50 to 500 mg, 50 to 400 mg, or 50 to 300 mg, more preferably 50 to 200 mg, based on once-daily administration to humans.

The compounds of the present invention may be administered by a conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the present compounds, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate hydrabamine, hydrobromide, hydrochloride, hydrogencarbonate, hydroxynaphtoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, diethyleneamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention can be formulated such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skills can easily determine and prescribe dosages that are effective for the desired treatment or prophylaxis. The medicament or pharmaceutical composition according to one embodiment may be administered in one or more doses, for example, one to four times per day. The pharmaceutical composition according to one embodiment may contain 50 to 500 mg, preferably 50 to 400 mg, more preferably 50 to 300 mg, and more preferably 50 to 200 mg of the compound of Formula 1.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivative (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the term "subject" refers to an animal that is the object of prevention or treatment, preferably a mammal (e.g., primates (e.g., ahuman), cattle, sheep, goats, horses, dogs, cats, rabbits, rats, mice, etc.), most preferably a human.

Effect of the Invention

The medicaments and pharmaceutical compositions according to the present invention can effectively prevent headaches, more particularly chronic headaches associated with cortical spreading depression (CSD), including migraine. In addition, the medicaments and pharmaceutical compositions according to the present invention do not affect the normal cerebral blood circulation or synaptic transmission.

DETAILED DESCRIPTION

Figure 1:
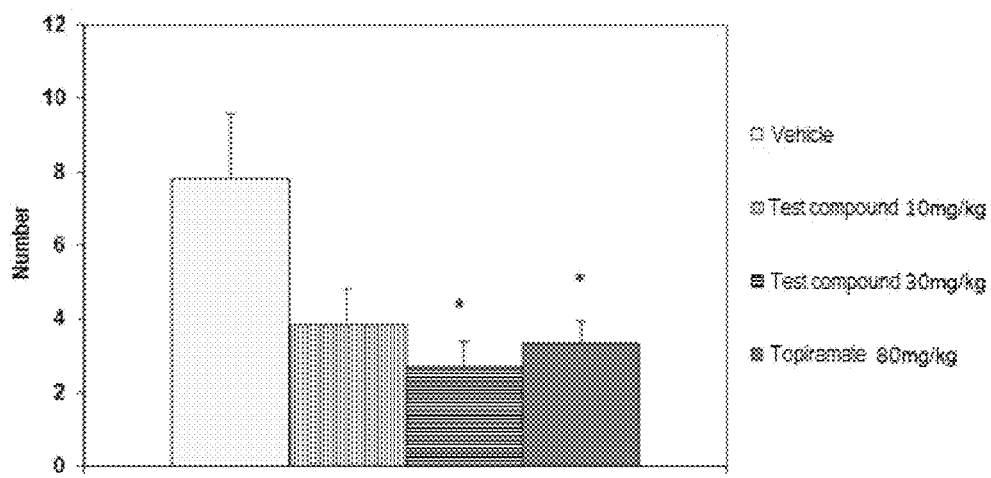
FIG. 1 shows the results of measuring the change in the number of events of increased cerebral blood flow (CBF) compared with the vehicle-administered negative control group, after inducing cortical spreading depression (CSD) in rats which were administered carbamic acid (R)-1-(2-chlorophenyl)-2-tetrazol-2-yl)ethyl ester prepared in the synthesis example (hereinafter referred to as "the test compound") and the positive control compound Topiramate for 3 weeks.

Hereinafter, the present invention will be explained in more detail through working examples. However, the following working examples are only intended to illustrate one or more embodiments and are not intended to limit the scope of the invention.

Synthesis Example: Synthesis of carbamic acid (R)-1-(2-chlorophenyl)-2-tetrazol-2-yl)ethyl ester Carbamic acid (R)-1-(2-chlorophenyl)-2-tetrazol-2-yl) ethyl ester was prepared according to the method described in Synthesis Example 50 of PCT Publication No. WO 2010/150946.

Example: Inhibitory Effect of Cortical Spreading Depression (CSD) Using Animal Model of Migraine Disease Caused by Cortical Spreading Depression (CSD) and Migraine-Prevention Pharmacological Effect Experiment All animal experiments were conducted in accordance with the National Institutes of Health (NIH) guidelines for the protection and use of laboratory animals and were approved by the State National Animal Experiment Board of Finland. A total of 48 adult male Wistar rats weighing 250 to 350 g were purchased from Charles River (Germany) and used in this experiment. The animals were raised at ambient temperature ($22\pm1°$ C.) under an environment in which food and water could be consumed arbitrarily and lighting was controlled (illuminated from 7 am to 8 pm). The animals were divided into the following four groups:

Twelve rats as a negative control group which were intraperitoneally administered 30% PEG400 (5 ml/kg) only, the vehicle of administration, once a day for three weeks
  Twelve rats which were intraperitoneally administered the test compound at a dose of 10 mg/kg once a day for three weeks
  Twelve rats which were intraperitoneally administered the test compound at a dose of 30 mg/kg once a day for three weeks
  Twelve rats as a positive control which were intraperitoneally administered Topiramate at a dose of 80 mg/kg once a day for three weeks On the last day of the three weeks of administration of the compound and the vehicle (30% PEG 400), the rats were anesthetized with 5% isoflurane (70% N2O and 30% O2 included, dose rate of 300 ml/min) and then were fixed to a stereotactic frame to perform the following surgery. During surgery, the concentration of anesthetic was reduced to 1 to 1.5%, and the rectal temperature was maintained at 37.0±1.0° C. using the homeothermic blanket system.

The skin of the rat head was incised and tilted to both sides, and the right hemisphere of the open skull was drilled using a drill to make three holes, the positions of which are as follows and are indicated by "mm" distance from the bregma; (1) in the occipital cortex, 4.5 at the rear and 2.0 at the lateral; (2) in the parietal cortex, 0.5 at the rear and 2.0 at the lateral; (3) in the frontal cortex, 2 at the front and 2 at the lateral. A laser-Doppler flow probe (Oxyflow, Oxford Optronics, UK) for monitoring the cerebral blood flow (CBF) and an invasive Ag/AgCl electrode for measuring the direct current (DC) potential change were placed on the uninjured dura of the holes drilled in the parietal and frontal cortex and within the cortex, respectively.

The laser-Doppler flow probes were placed in areas with no large pial and dural blood vessels to minimize the interference of the large vessels to the signal. For the measurement of the DC potential difference, a reference electrode was fixed to the neck. The dura on the occipital cortex was carefully removed and care was taken to minimize bleeding. After surgery, the cortical area was restored by washing with saline for 15 minutes. Sphere-shaped (2 mm diameter) cotton wool was wetted with 1 M KCl solution and placed on the pia, and 5 µl of KCl solution was added thereto every 15 minutes to prevent drying. The occurrence of KCl-induced cortical spreading depression (CSD) was measured for 2 hours.

Cerebral blood flow (CBF) and DC potential were continuously monitored starting 5 minutes before KCl treatment. The last drug administration took place 30 minutes before the KCl solution treatment. The parameters analyzed were (1) the number of events of DC potential, the duration of the event, the magnitude of amplitude, and (2) the number of events of cerebral blood flow change and the size of the magnitude of change. All values were expressed as mean±standard error of mean (SEM), and statistical significance was recognized when data had a difference of $P<0.05$. Statistical analysis was performed using unpaired t-test on StatsDirect statistical software.

Figure 2:
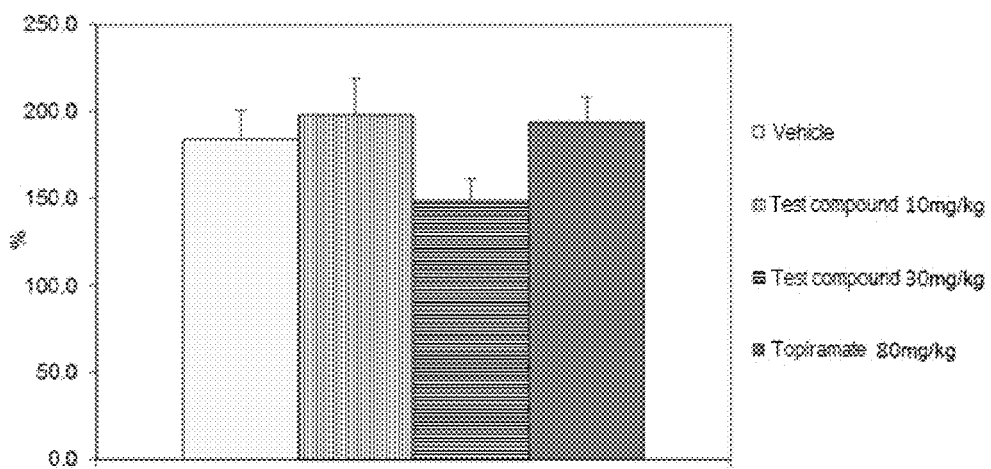
FIG. 2 shows the results of measuring the change in the degree of increased cerebral blood flow compared with the vehicle-administered negative control group, after inducing cortical spreading depression (CSD) in rats which were administered the test compound and the positive control compound Topiramate for 3 weeks.
Figure 3:
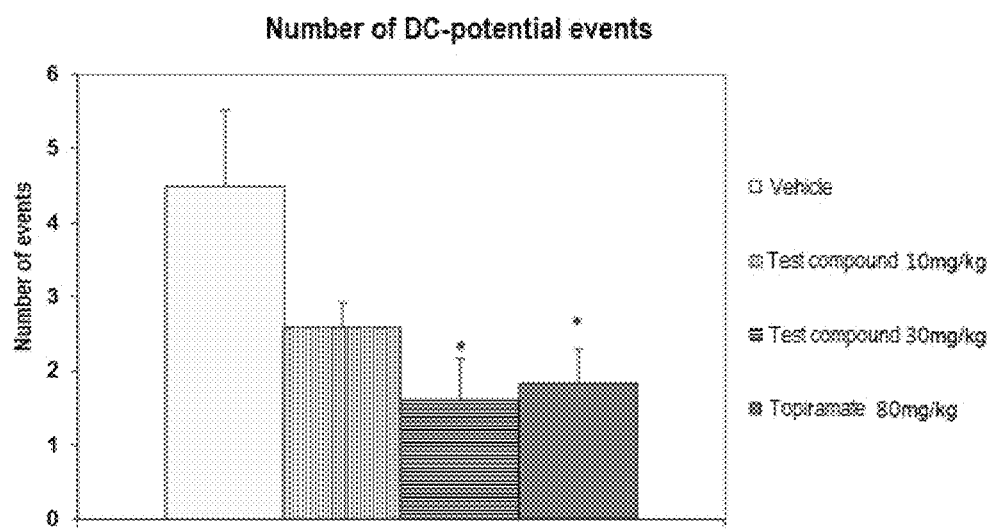
FIG. 3 shows the results of measuring the change in the number of events of direct current (DC) potential compared with the vehicle-administered negative control group, after inducing cortical spreading depression (CSD) in rats which were administered the test compound and the positive control compound Topiramate for 3 weeks.
Figure 4:
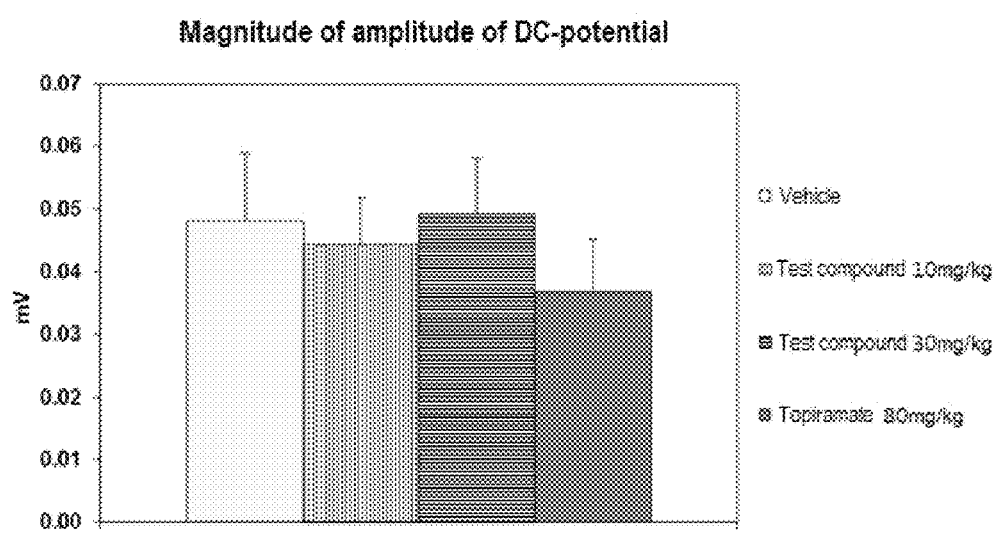
FIG. 4 shows the results of measuring the degree of the magnitude of amplitude of direct current (DC) potential compared with the vehicle-administered negative control group, after inducing cortical spreading depression (CSD) in rats which were administered the test compound and the positive control compound Topiramate for 3 weeks.
Figure 5:
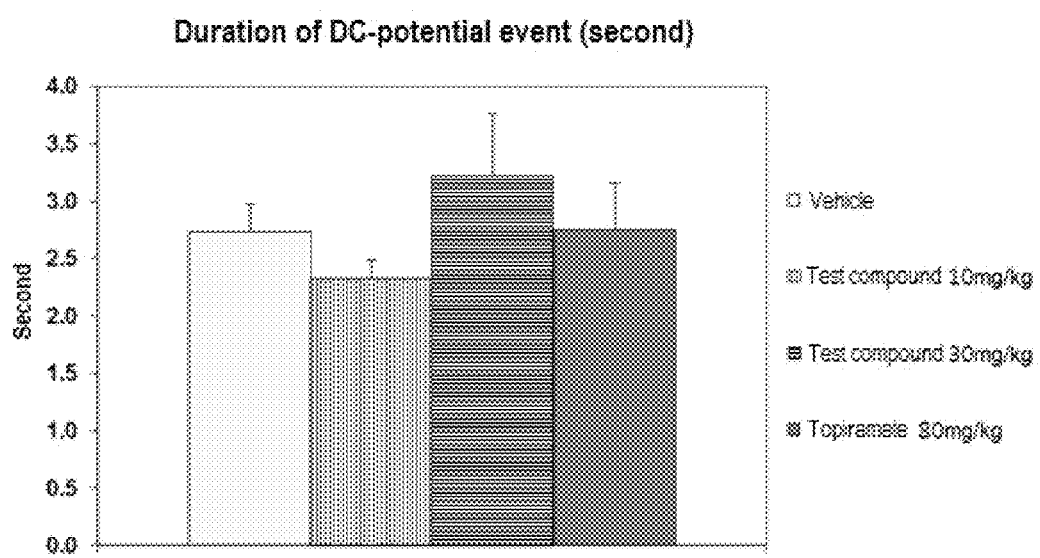
FIG. 5 shows the results of measuring the duration of event of direct current (DC) potential compared with the vehicle-administered negative control group, after inducing cortical spreading depression (CSD) in rats which were administered the test compound and the positive control compound Topiramate for 3 weeks.

After inducing cortical spreading depression (CSD) in the rats which were administered the above compound and the vehicle, the changes in cerebral blood flow (CBF) and the changes in DC potential were measured, the results of CBF measurement are shown in FIG. 1 and FIG. 2, and the results of DC potential measurement are shown in FIG. 3, FIG. 4 and FIG. 5.

The test compound significantly reduced the number of events of increased cerebral blood flow at a dose of 30 mg/kg compared to the vehicle treated group (negative control) (FIG. 1). The effect was a level similar to the reduction effect shown by Topiramate at the high dose of 80 mg/kg on the number of events of increased cerebral blood flow. However, the test compound showed no significant effect on the degree of cerebral blood flow increase, indicating that it has no effect on normal cerebral circulation (FIG. 2). In addition, the test compound significantly reduced the number of DC-potential events at a dose of 30 mg/kg compared to the vehicle treated group, and this effect was a level similar to the effect shown by Topiramate at 80 mg/kg (FIG. 3). However, the test compound had no significant effect on the magnitude of amplitude and the duration of the DC-potential event, indicating that it does not affect normal synaptic transmission (FIG. 4 and FIG. 5).

The above results show that the present compounds (the test compound) exhibit sufficient pharmacological effects of improving migraine headache indicators and preventing the cortical spreading depression (CSD) phenomenon in migraine disease models at low doses compared to Topiramate, and thus it could be confirmed that the present compounds are useful as drugs for the prevention of migraine headaches.

What is claimed is:

1. A method for prophylactically treating headaches in a subject, comprising:
   administering a therapeutically effective amount of a carbamate compound of Formula 1, or a pharmaceutically acceptable salt, solvate or hydrate thereof to the subject:

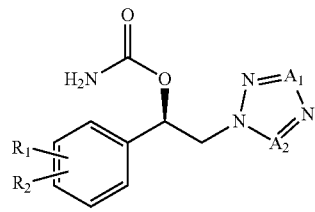

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl)ethyl ester of Formula 2:

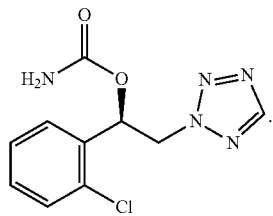

[Formula 2]

4. The method according to claim 1, wherein the headache is headache associated with cortical spreading depression (CSD).

5. The method according to claim 1, wherein the headache is chronic headache.

6. The method according to claim 1, wherein the headache is migraine.

7. The method according to claim 6, wherein the migraine is migraine with aura.

8. The method according to claim 1, wherein the subject is a mammal.

9. The method according to claim 8, wherein the mammal is a human.

10. The method according to claim 1, wherein the therapeutically effective amount of the carbamate compound of Formula 1 is 10 to 500 mg based on once-daily administration.

11. The method according to claim 1, wherein the carbamate compound of Formula 1, or a pharmaceutically acceptable salt, solvate or hydrate thereof is administered orally, parenterally, intravenously, intramuscularly, subcutaneously or rectally.

* * * * *